United States Patent
Ahn et al.

(10) Patent No.: US 7,079,890 B2
(45) Date of Patent: Jul. 18, 2006

(54) ELECTROCHEMICAL THERAPY APPARATUS

(75) Inventors: Saeyoung Ahn, Seoul (KR); Hong Bae Kim, Seoul (KR); Seo Kon Kim, Seoul (KR)

(73) Assignee: Solco Biomedical Co., Ltd., Kyungki-do (KR)

( * ) Notice: Subject to any disclaimer, the term of this patent is extended or adjusted under 35 U.S.C. 154(b) by 48 days.

(21) Appl. No.: 10/803,866

(22) Filed: Mar. 18, 2004

(65) Prior Publication Data

US 2004/0186518 A1    Sep. 23, 2004

Related U.S. Application Data

(60) Provisional application No. 60/455,949, filed on Mar. 19, 2003.

(30) Foreign Application Priority Data

May 28, 2003  (KR) ...................... 10-2003-0034037
May 28, 2003  (KR) ...................... 10-2003-0034038

(51) Int. Cl.
    *A61N 607/03*    (2006.01)
(52) U.S. Cl. ............................... 607/3; 607/2; 607/115
(58) Field of Classification Search .................... 607/1, 607/2, 50, 66, 67, 75, 133, 138, 148
    See application file for complete search history.

(56) References Cited

U.S. PATENT DOCUMENTS

| 4,026,304 A | 5/1977 | Levy .......................... 128/419 |
| 4,289,135 A | 9/1981 | Nordenström et al. ...... 128/419 |
| 4,572,214 A | 2/1986 | Nordenström et al. ...... 128/785 |
| 4,679,561 A | 7/1987 | Doss .......................... 128/422 |
| 4,919,138 A | 4/1990 | Nordenström ............... 128/421 |
| 4,974,595 A | 12/1990 | Nordenström ............... 128/642 |
| 5,088,981 A * | 2/1992 | Howson et al. ................ 604/31 |
| 5,098,843 A | 3/1992 | Calvin ........................ 435/287 |

(Continued)

OTHER PUBLICATIONS

K Li et al, Effects of Direct Current on Dog Liver: Possible Mechanisms for Tumor Electrochemical Treatment, 1997, Wiley, vol. 18 Issue 1, pp. 2-7.*

*Primary Examiner*—Robert E Pezzuto
*Assistant Examiner*—Brian T. Gedeon
(74) *Attorney, Agent, or Firm*—Baker Botts LLP

(57) ABSTRACT

The present invention relates to an electrochemical therapy apparatus in which various tumors such as cancers are treated using an electrochemical method that utilizes an interaction between an anodic electrode and a cathodic electrode. The electrochemical therapy apparatus includes a main controller for performing calculation processes of parameters for electrochemical therapy; a storage unit connected to the main controller, and storing a program for processing the parameters and also storing data related to the parameters; an input unit and an output unit connected to the main controller, the output unit displaying or printing data related to the parameters; a converter connected to the main controller and converting the parameters output from the main controller into analog values to transmit the parameters as electrical signals for electrochemical therapy, or converting input analog values into digital values and transmitting the digital values as electrical signals to the main controller; a plurality of channels connected to the converter to transmit electrical signals, each of the channels operating independently; and a plurality of electrode units each connected to one of the channels, and each including an anodic electrode and a cathodic electrode in a wire shape, and that are coated with platinum and between which direct current flows to perform electrochemical therapy.

15 Claims, 6 Drawing Sheets

U.S. PATENT DOCUMENTS

| | | | |
|---|---|---|---|
| 5,501,662 A | 3/1996 | Hofmann | 604/20 |
| 5,584,872 A | 12/1996 | LaFontaine et al. | 607/116 |
| 5,630,426 A | 5/1997 | Eggers et al. | 128/734 |
| 5,820,548 A | 10/1998 | Sieben et al. | 600/361 |
| 5,861,002 A * | 1/1999 | Desai | 606/210 |
| 6,021,347 A * | 2/2000 | Herbst et al. | 607/2 |
| 6,161,048 A * | 12/2000 | Sluijter et al. | 607/100 |
| 6,235,024 B1 * | 5/2001 | Tu | 606/41 |
| 6,366,808 B1 | 4/2002 | Schroeppel et al. | 607/2 |
| 6,521,462 B1 * | 2/2003 | Tanouye et al. | 436/149 |
| 6,574,507 B1 * | 6/2003 | Bonnet | 607/20 |
| 6,638,277 B1 * | 10/2003 | Schaefer et al. | 606/41 |
| 6,738,663 B1 * | 5/2004 | Schroeppel et al. | 607/2 |
| 6,826,429 B1 * | 11/2004 | Johnson et al. | 607/67 |
| 6,853,863 B1 * | 2/2005 | Carter et al. | 607/69 |
| 6,892,086 B1 * | 5/2005 | Russell | 600/372 |
| 6,901,296 B1 * | 5/2005 | Whitehurst et al. | 607/50 |
| 6,919,168 B1 * | 7/2005 | Hwang et al. | 430/318 |

* cited by examiner (A)

(B)

(C)

(A)

(B)

(A)

(B)

ELECTROCHEMICAL THERAPY APPARATUS

CROSS-REFERENCE

This application is related to the provisional application filed on Mar. 19, 2003, Ser. No. 60/455,949, entitled "Electrochemical Therapy Equipment." In addition, the present application contains subject matter related to Korean patent application Nos. 2003-0034037 and 2003-0034038, filed in the Korean Industrial Patent Office on May 28, 2003, the entire contents of which being incorporated herein by reference. Priority under 35 U.S.C. § 119 to these applications has been claimed.

BACKGROUND OF THE INVENTION

1. Field of the Invention

The present invention relates to an electrochemical therapy apparatus, and more particularly, to an electrochemical therapy apparatus in which various tumors such as cancers are treated using an electrochemical method that utilizes an interaction between an anodic electrode and a cathodic electrode.

2. Description of the Related Art

Cancer is a serious disease that threatens the health of modern-day citizens. Cancer destroys healthy cells by cell mutation or multiplication, the end result of which may be death to the patient. Methods to treat cancerous tumors include a surgical method in which the tumor is excised, a method in which tissue is destroyed by directing radioactive rays onto the tumor, and a method in which cancer cells are destroyed using a cancer-inhibiting drug.

Although the surgical method of excising the tumor is a secure method for a cancerous tumor in the early stages, there are significant risks involved when applying this procedure to malignant tumors. With respect to the method of destroying tissue by using radioactive rays on the tumor or the method of destroying cancer cells or using a cancer-inhibiting drug, although these methods are effective during the early stages of cancer, they are limited in their effectiveness when used to treat malignant tumors. In particular, these treatment methods cannot be used for patients that have become weak as a result of a reduced immunity.

Electrochemical treatment methods have been developed as an alternative to the above cancer treatment methods and to overcome the problems of the same. In the electrochemical treatment method, anodic electrodes and cathodic electrodes are inserted into the cancer and a small current is flowed between their terminals to thereby induce an electrochemical reaction and changes in acidity. These effects change the environment in which the cancer may survive, ultimately resulting in destroying the cancer. When an electric field is applied to the tumors located between the electrodes, $H_2O$ with dipole moment located inside and outside tumors are moved along the direction of the electric field. Therefore, dehydration happens in the vicinity area of the anodic electrodes while oedema happens in the vicinity area of the cathodic electrodes, such that the cancer cells are naturally destroyed.

SUMMARY OF THE INVENTION

The present invention relates to therapy equipment for treating cancer tumors by an electrochemical method. In the electrochemical therapy equipment of the present invention, an amount of electric charge, current intensity of a direct current and voltage are suitably adjusted and applied depending on the size of a tumor such that an electrochemical reaction and a biological reaction are induced to destroy cancer cells, and reduce the size of the tumor and even completely remove the same.

The electrochemical therapy apparatus includes a main controller for performing calculation processes of parameters for electrochemical therapy; a storage unit connected to the main controller, storing a program for processing the parameters and also storing data related to the parameters; an input unit and an output unit connected to the main controller, and the output unit displaying or printing data related to the parameters; a converter connected to the main controller and converting the parameters output from the main controller into analog values to transmit the parameters as electrical signals for electrochemical therapy, or converting input analog values into digital values and transmitting the digital values as electrical signals to the main controller; a plurality of channels connected to the converter to transmit electrical signals, each of the channels operating independently; and electrode units each connected to one of the channels, and each including an anodic electrode and a cathodic electrode in a wire shape, and that are coated with platinum and between which direct current flows to perform electrochemical therapy.

Each of the channels may include an isolated amplifier, which is electrically isolated, outputs an electrical signal transmitted from the converter to realize independent driving for electrochemical therapy in order to prevent electrical shocking from transmitting to the patient, an output driver connected to the isolated amplifier, receiving a driving voltage for electrochemical therapy and converting the driving voltage to a direct current, and maintaining a constant current or a constant voltage for a predetermined time in step pattern, a protection unit connected to the electrode unit and cutting off power when there are abnormalities in the current or voltage applied to the electrode unit from the output driver; and a detector connected to the electrode unit, detecting a voltage or a current applied to the electrode unit, and transmitting the voltage or current to the converter.

Preferably, the output driver maintains the constant voltage of 2V for one hour and then generates a constant current of 100 mA.

The electrochemical therapy apparatus may further include a warning unit generating a warning message or warning alarm when a circuit in the electrode unit is open or short and a corresponding signal is received from the main controller.

The protection unit may further include a power cutoff circuit that receives a driving voltage from the corresponding electrode unit, and cuts off power supplied to the electrode unit if any one of a current and voltage between the anodic electrode and the cathodic electrode falls outside of the ranges respectively of 1~300 mA and 1~30V.

The protection unit may further include a power cutoff circuit that cuts off power supplied to the corresponding electrode unit when a resistance value, which is obtained by setting a distance between the anodic electrode and the cathodic electrode as a numerical value, exceeds a predetermined value.

The anodic electrodes and the cathodic electrodes may be made of tungsten, with surfaces thereof being rough.

Preferably, at least one of the anodic electrodes and the cathodic electrodes are coated with platinum using a non-equilibrium magnetron sputtering method.

Preferably, a thickness of the platinum coated on the anodic electrodes and the cathodic electrodes is 2500~3000 Å.

The electrode units may each include a distributor connected to the anodic electrodes and the cathodic electrodes.

Each of the distributors may include tweezer-like members or connecting tubes at one end thereof, and each is connected to the corresponding anodic electrode and cathodic electrode through the tweezer-like members or connecting tubes.

Preferably, the electrode units further include a guide cap that surrounds a distributor-connecting area of the anodic electrode and the cathodic electrode, and exposes an opposite end.

The electrochemical therapy apparatus may further include a flexible tube positioned along a lengthwise direction of the anodic electrode and the cathodic electrode between the anodic electrode and cathodic electrode of the distributor-connecting area and the guide cap, and a plurality of wire ties are formed surrounding an outer circumference of the flexible tube at predetermined intervals, part of the guide cap in the area where the wire ties are formed being cut away.

The wire ties may alternately have a positive polarity and a negative polarity formed thereon.

Preferably, at least one of the anodic electrodes and the cathodic electrodes is wave shaped or coil shaped.

BRIEF DESCRIPTION OF THE DRAWINGS

The accompanying drawings, which together with the specification, illustrate exemplary embodiments of the present invention, and, together with the description, serve to explain the principles of the present invention.

DETAILED DESCRIPTION OF THE INVENTION

Embodiments of the present invention will now be described in detail with reference to the accompanying drawings.

Figure 1:
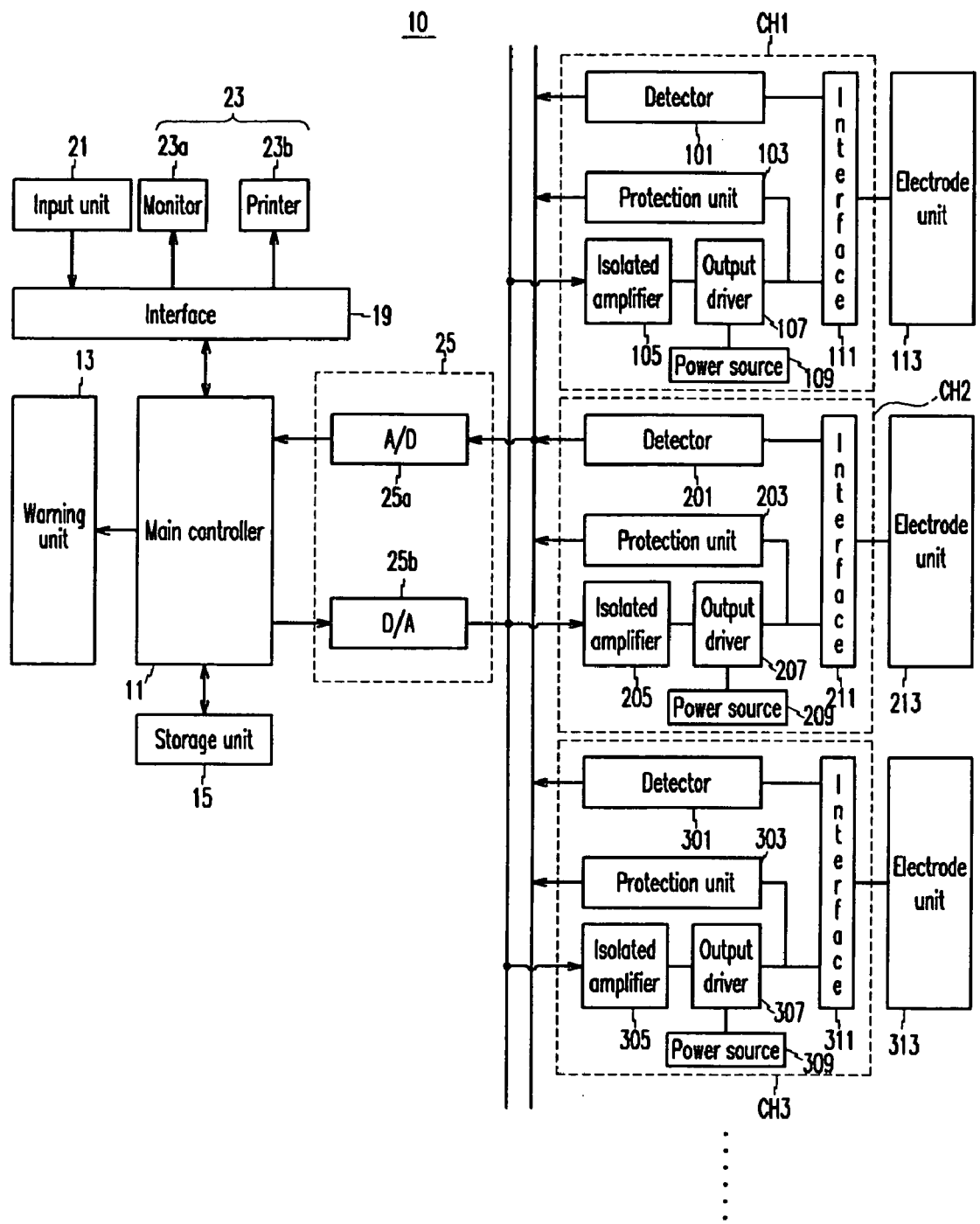
FIG. 1 is a schematic block diagram of an electrochemical therapy apparatus according to an embodiment of the present invention.

FIG. 1 is a schematic block diagram of an electrochemical therapy apparatus according to an embodiment of the present invention. As shown in FIG. 1, main elements of the electrochemical therapy apparatus 10 according to an embodiment of the present invention include a main controller 11 for performing calculation processes of parameters for electrochemical therapy; a storage unit 15 connected to the main controller 11, storing a program for processing the parameters and also storing data related to the parameters; an input unit 21 and an output unit 23 connected to the main controller 11, the output unit 23 either displaying or printing data related to the parameters; a converter 25 connected to the main controller 11 and converting the parameters output therefrom into analog values to transmit the parameters as electrical signals for electrochemical therapy, or converting input analog values into digital values and transmitting the digital values as electrical signals to the main controller 11; a plurality of channels (CH1, CH2, . . . ) connected to the converter 25 to transmit electrical signals, each of the channels (CH1, CH2, . . . , ) operating independently; and electrode units (113, 213, . . . ) connected respectively to the channels (CH1, CH2, . . . ), and each including an anodic electrode and a cathodic electrode coated with platinum and between which direct current flows to perform electrochemical therapy.

The main controller 11 controls each of the elements connected thereto using electrochemical therapy parameters input through the input unit 21, and processes the parameters input through the input unit 21 using an internal arithmetic processing circuit.

The storage unit 15 includes a storage circuit that is a magnetically recorded, and stores an operation control program for operating the electrochemical therapy apparatus. The operation control program includes a diagram description program, an injection simulation program, a case history management program, a result recording program, and a specialist guidance program.

The diagram description program is a program used to describe the use and the clinical trial effect of the electrochemical apparatus in the form of diagrams. Inspection evaluation, simple introduction to the program, pathology description, and explanation of operation are put in diagram form to provide specific information to users. Further, the program shows a certain number of treatment cases to provide information to the users in a form that allows for easy comparison between diagrams.

The injection simulation program performs an injection simulation of tumors based on electrochemical therapy parameters that are input by users, and provides theoretical maximum values of electric charge amounts.

The case history management program manages the case histories of patients receiving therapy. In particular, it is possible to input, examine, and delete case histories. Also, the case histories may be divided by introduction and content to allow for searching and editing.

The result recording program shows patient's name, the number of treatments, and the electrochemical therapy parameters. The electrochemical therapy parameters include voltage, current, electric charge, tumor size, and resistance value. This allows for verification of statistical analysis results based on past therapy results.

The specialist guidance program provides the method of operating the electrochemical therapy apparatus, the method of using a database, and also provides specialist suggestions.

These programs are loaded to the main controller 11 from the storage unit 15 such that a voltage, current, and electric charge needed for the particular size of the tumor are automatically calculated. A simulation is then performed with respect to optimum electrode placement and anodic electrodes and cathodic electrodes arrangement. In addition, the programs inform users of open and short states of the electrodes if they occur, and allow for one of the voltage and current to be fixed and the other to be varied. The programs also record and store case histories to manage the same.

As an example, a keyboard that allows the input of electrochemical parameters may be used as the input unit 21. The output unit 23 may include a monitor 23a or a printer 23b, the monitor 23a allowing for the display of electrochemical parameters and showing corresponding calculation results of patient case history and therapy history. The input unit 21 and the elements included in the output unit 23 merely illustrate the present invention and are not meant to be restrictive. As shown in FIG. 1, an interface 19 is provided between the input unit 21 and the main controller 11 and between the output unit 23 and the main controller 11. The interface 19 allows for the easy exchange of electrochemical therapy data between the main controller 11 and these elements.

The converter 25 includes a digital-to-analog converter 25a (hereinafter referred to as a "D/A circuit") for converting digitized parameters for performing electrochemical therapy of cancer into analog values and supplying the result to each of the channels. The converter 25 also includes an analog-to-digital converter 25b (hereinafter referred to as an "A/D circuit") receiving analog data of electrochemical therapy from each of the channels and digitizing the data, then supplying the digitized data as parameters for electrochemical therapy to the main controller 11. Hence, by digitizing the parameters needed for electrochemical therapy, and, at the same time, freely performing modification of physical analog data through the converter 25, the data processing speed in real-time is increased and variations in cancerous tumors may be verified in real-time.

In addition, the electrochemical therapy apparatus 10 of the present invention further includes a warning unit 13. In the event an open or short occurs in the anodic electrode or the cathodic electrode of the electrode units, the warning unit 13 receives an electric signal indicating this fact from the main controller 11 and generates a warning message or a warning alarm. The warning unit 13 includes a warning circuit to perform this function.

The electrochemical therapy apparatus 10 of the present invention uses a plurality of channels and an electrode unit connected to each of the channels to realize a more improved effectiveness in treating cancerous tumors. In FIG. 1, although three channels CH1, CH2 and CH3, and three corresponding electrode units 113, 213, and 313 are shown, this number of channels and electrode units is used for illustrative purposes only and is not meant to limit the present invention. Accordingly, a greater number of the channels and electrode units may be provided. In the following, an embodiment of the present invention will be described by providing an explanation of the channel CH1 and the electrode unit 113. Since the following explanation of the channel CH1 and the electrode unit 113 may be applied to the other channels (CH2, CH3, ...) and the other electrode units (213, 313, ...), a detailed explanation of the other channels and electrode units will not be provided.

In the present invention, there are provided a plurality of channels, each of which comprises a closed circuit and includes isolated amplifiers, and an electrode unit is connected to each of the channels. Therefore, by such independent operation, safety is increased during therapy as is the effectiveness of treatment. Also, by applying electrical signals to the treatment area through such independent operation, interference between channels is prevented, and the effectiveness of treatment is maximized as a result of performing treatment by each individual electrode unit.

The channel CH1 connected to the electrode unit 113 includes an isolated amplifier 105, which is electrically isolated, outputs an electrical signal transmitted from the converter 25 to realize independent operation for electrochemical therapy; an output driver 107 connected to the isolated amplifier 105, receiving a driving voltage for electrochemical therapy and converting it into a direct current, and maintaining a constant current or a constant voltage for a predetermined time in step pattern; a protection unit 103 connected to the electrode unit 113 and cutting off power when there are abnormalities in the current or voltage applied to the electrode unit 113 from the output driver 107; and a detector 101 connected to the electrode unit 113, detecting a voltage or a current applied to the electrode unit 113, and transmitting the voltage or current to the converter 25. Each of these elements sends and receives electrical signals to and from the electrode unit 113 through an interface 111. In the present invention, the channel CH1 includes the isolated amplifier 105 to thereby realize independent driving so that interference with other channels is avoided.

The detector 101 includes a current detection circuit for detecting an output current flowing to the electrode unit 113, and a voltage detection circuit for detecting an output voltage applied to the electrode unit 113. The detector 101 converts the detected current or voltage into a signal form, and transmits the signal to the A/D circuit 25a of the converter 25. As an example, a plurality of temperature sensors may be inserted into the treatment area and the temperature sensors may be connected to the detector 101 through the interface 111. As a result, the detector 101 is able to determine temperature changes in the area of treatment to thereby determine how much the surgery has progressed.

The protection unit 103 plays the important role of protecting the human body in that the present invention is a device used on the human body. The protection unit 103 detects a current and voltage applied to the electrode unit 113 to prevent overcurrent from flowing to the treatment area or overvoltage from being applied thereto. Accordingly, the protection unit 103 includes a power cutoff circuit for discontinuing the supply of power to the electrode unit 113 in the case where the current and voltage of the anodic electrode and cathodic electrode fall outside a predetermined range. This is also the case when the voltage becomes 0 as a result of the anodic electrode contacting the cathodic electrode (i.e., as a result of a short between the electrodes). The protection unit 103 also includes a power cutoff switch to allow for the manual cutoff of power.

The current and voltage between the anodic electrode and cathodic electrode may be adjusted within the ranges respectively of 1~300 mA and 1~30V. If either or both the current and the voltage fall outside these ranges, the power cutoff circuit performs cutoff of the power supplied to the electrode unit 113.

If the current flowing between the anodic electrode and the cathodic electrode is less than 1 mA, there is only a minimal effectiveness of the electrochemical therapy. Also, a current that exceeds 300 mA between the positive and cathodic electrodes is dangerous to the patient. Similarly, a voltage of less than 1V between the anodic electrode and the cathodic electrode is such that the difference in potential between the electrodes is too small to realize an electrochemical therapy effect, while a voltage that is greater than 30V between the electrodes is dangerous to the patient.

Varying the distance between the anodic electrode and the cathodic electrode results in large differences in the effectiveness of electrochemical therapy. As a result, the electrochemical therapy apparatus 10 of the present invention sets as a numerical resistance value the distance between the anodic electrodes and cathodic electrodes, and uses this as a parameter. Accordingly, if the distance between the anodic electrode and the cathodic electrode exceeds a predetermined amount (i.e., if the resistance value increases to above a predetermined value), the protection unit 103 performs cutoff of the power supplied to the electrode unit 113 to thereby prevent the flow of unneeded current to the treatment area. Such a situation may also be indicated through the warning unit 13. Preferably, the predetermined value of the resistance value is approximately 25 kΩ.

The isolation amplifier 105 that is connected to the converter 25 to receive analog signals converted in the D/A circuit 25b is an element that electrically isolates and outputs analog signals. The isolation amplifier 105 is mounted to prevent the crossing of wires with other channels in order to ensure the safety of patients receiving electrochemical therapy. Therefore, each of the channels is independently driven and independently grounded.

The output driver 107, which is connected to the isolated amplifier 105, receives a driving voltage from a power source 109 and converts digital values into direct current, and current or voltage applied through electrodes is either amplified or attenuated before being transmitted to the electrode unit 113 through the interface 111. The output driver 107 adjusts output current to 1~300 mA and output voltage to 1~30V. More preferably, the output driver 107 adjusts output current to 1~150 mA and output voltage to 1~20V.

Figure 2:
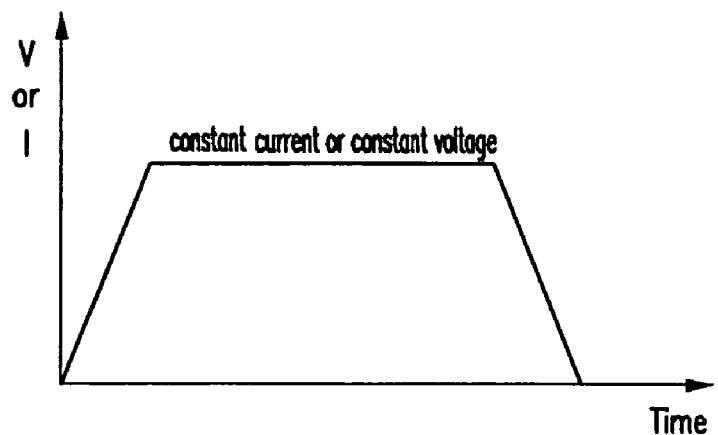
FIG. 2 is a graph showing various changes in output current and voltage as a function of time according to a pattern input to an output driver.
Figure 2:
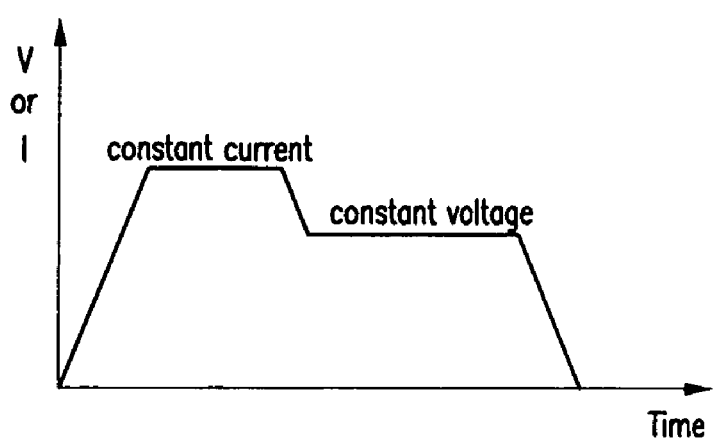
Figure 2:
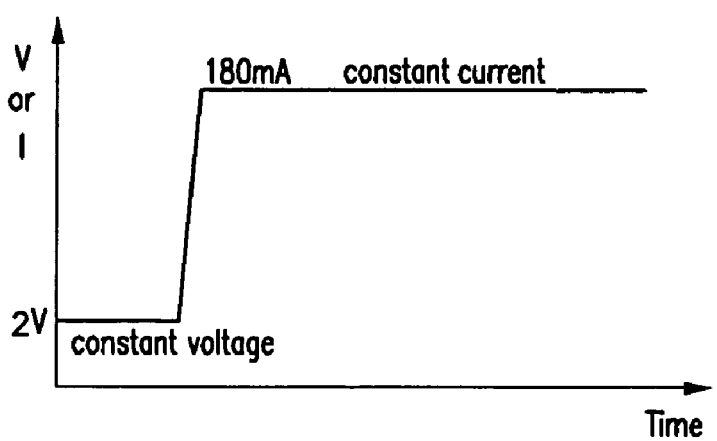

In the present invention, a therapy pattern function is input to the output driver 107 such that an output amount and time of a constant voltage and a constant current are uniformly adjusted according to a predetermined pattern. It is desirable to diversify electrochemical therapy methods according to the kinds and locations of the tumors. Therefore, the constant voltage and constant current are optimized for a predetermined time in a step pattern to thereby maximize the effectiveness of therapy and also to allow the effectiveness of therapy to be predicted so that electrochemical therapy is made more convenient. FIG. 2 is a graph showing various changes in output current and voltage as a function of time according to a pattern input to the output driver 107. As shown in FIG. 2, voltage or current may be uniformly maintained in step according to a previously input pattern. This may be varied as needed to perform electrochemical therapy.

As shown in FIG. 2(A), it is possible to increase current or voltage constantly in time, respectively and then maintain them the same, respectively. Also, as shown in FIG. 2(B), it is possible to maintain current constantly and then maintain voltage constantly. On the contrary, as shown in FIG. 2(C), it is possible to maintain the voltage constantly and then maintain the current constantly. These patterns are used for illustrative purposes only and are not meant to limit the present invention.

These methods are accomplished by the software which is shown on the monitor of the electrochemical therapy apparatus of the present invention. In the software, basic pattern icons are given, and current pattern and voltage pattern are constituted by dragging the basic pattern icons. The basic pattern icons are constituted in step, which maintains a current or a voltage constantly or increases a current or a voltage linearly. It is possible to control at least one of a voltage, current and time by making basic sections in a working window and adjusting them such as raising, lowering, extending or shortening.

Especially, as shown in FIG. 2(C) of the present invention, it is desirable to maintain a voltage under 2V for one hour and then set a constant current of 110 mA. Therefore, the effect of electrochemical therapy can be improved. It is desirable to maintain the constant voltage 2V for one hour and maintain a slight current such as 1~10 μA in order not to induce electrochemical reaction near the electrodes. Then, after one hour, electrochemical reaction is drastically induced by raising the voltage above 2V.

The area of treatment undergoes therapy using the electrode units connected to each channel. The electrode units are realized through an anodic electrode and a cathodic electrode in the form of a wire that is coated with platinum. Reference electrodes may also be inserted into the treatment area. By measuring a voltage and current strength between the anodic electrodes and cathodic electrodes using the reference electrodes, it is possible to refer the result of measurement in the treatment process and treatment progress.

After the anodic electrode and cathodic electrode are inserted into the area of treatment with a gap of 3 cm or less provided therebetween, a direct current is flowed between the electrodes. The direct current may be typical direct current or may be pulse current that is transmitted by placing a pulse on a bias voltage. In the latter case, a pulse width of the pulse current is between 50 ns and 100 ms, and the bias voltage is between 0.5 kV and 3 kV. The direct current, voltage, and electric charge amount are proportional to the size and volume of the tumor, and also vary depending on the position of the tumor. The average amount of electric charge needed is approximately 100 C per 1 cm in length of the tumor.

If direct current is flowed to the area of treatment, $H_2O$ with a dipole moment in tumors is moved from the anodic electrode to the cathodic electrode along the direction of an electric field generated between the electrodes. As a result, the area around the anodic electrode becomes dehydrated while the area in the vicinity of the cathodic electrode experiences oedema. The dehydrated area and the oedema area are a result of the body fluids moving in the direction of the electric field from the anodic electrode to the cathodic electrode, and induce a disruption in metabolism to thereby destroy the tumor cells.

When direct current flows through tumor tissue, the pH value is changed as a result of the electrochemical reaction at the electrodes. That is, anions ($H^+$, $Na^+$, etc.) move toward the cathodic electrode, while cations ($Cl^-$, etc.) move toward the anodic electrode. The following chemical reactions occur as a result.

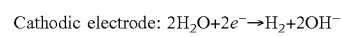
Cathodic electrode: $2H_2O + 2e^- \rightarrow H_2 + 2OH^-$

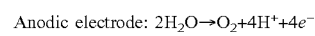
Anodic electrode: $2H_2O \rightarrow O_2 + 4H^+ + 4e^-$

where $4H^+ + 4H_2O^- \rightarrow 4H_3O^+$

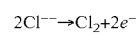
$2Cl^- \rightarrow Cl_2 + 2e^-$

Although $OH^-$ is created in the cathodic electrode, it is not generated in the anodic electrode. Accordingly, the area in the vicinity of the anodic electrode becomes highly acidic while the area in the vicinity of the cathodic electrode becomes highly alkaline. High acidity and high alkalinity act to destroy tumor tissues. $Cl_2$ generated in the anodic electrodes destroy the tumor tissues with its strong virulence.

A depolarization of the tumor cell membrane induces a disruption in metabolism. That is, the environment within the cells comes to have more of a negative electric charge than the environment outside the cells. This indicates that the cells have a stable membrane potential difference as a result of ion concentration gradient of the structural material. If the difference in potential of the tumor cells is abruptly reduced, a difference in density occurs. Direct current changes the ion concentration, and in particular the ion density outside the cells such that the difference in electric potential is also changed. The difference in potential affects the movement of ions to thereby effect repolarization of the cell membranes, ultimately resulting in destroying tumor cells.

Further, if the anodic electrode and the cathodic electrode are inserted in the area of treatment and then a direct current flows therebetween, and an electrochemical reaction is generated in the treatment area such that dielectric features are exhibited at the electrodes where dielectric features have not been exhibited, and the dielectric features are calculated from the direct current such that therapy progress and therapy state may be determined.

In addition, after specific rays of light are irradiated onto the tumor, changes in reflexibility differences are detected so that it may be ascertained whether there have been any changes in the properties of the tumor tissue. Also, after injecting materials that react to specific rays of light into the tissue of the tumor, any differences may be detected in accordance with the changes in the tissue of the tumor following therapy.

In the following, first through fourth embodiments will be described with respect to the electrode unit of the electrochemical therapy apparatus of the present invention that causes an electrochemical reaction following direct contact to the treatment area. These embodiments merely illustrate the present invention and are not meant to be restrictive.

An electrode unit of the electrochemical therapy apparatus according to an embodiment of the present invention includes the main elements of a distributor and an electrode connected thereto. The distributor transmits to electrodes a driving voltage applied through tweezer-like members connected to a positive terminal and a negative terminal, or applied through connecting tubes. As a result, an electrochemical reaction is induced between the anodic electrode and the cathodic electrode.

Figure 3:
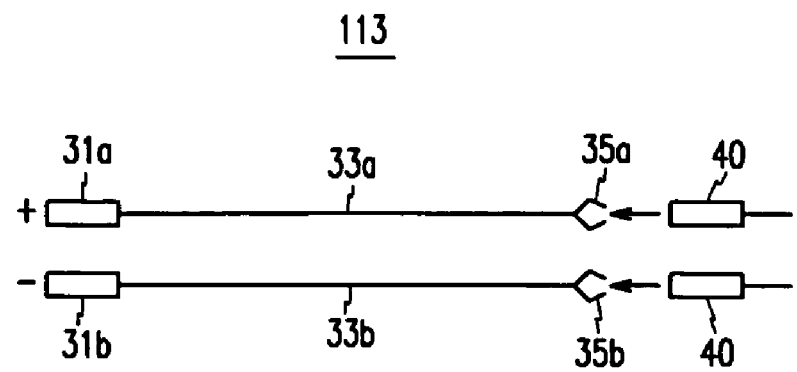
FIG. 3 is schematic views of a distributor of an electrode unit in an electrochemical therapy apparatus according to an embodiment of the present invention.
Figure 3:
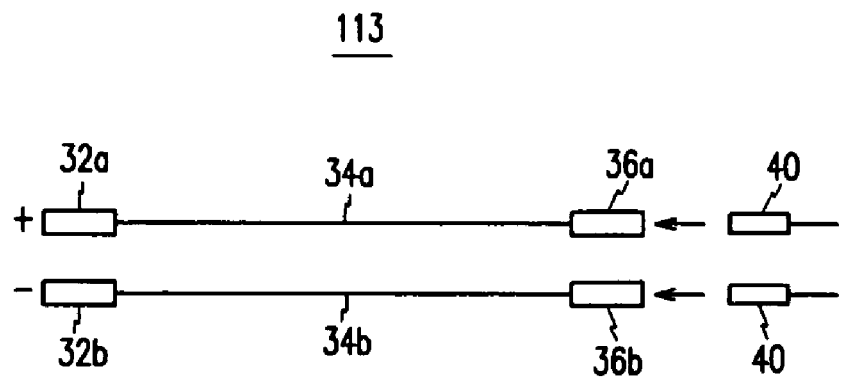

FIG. 3 shows schematic views of distributors of an electrode unit and connections of the distributors with electrodes according to an embodiment of the present invention. In FIG. 3, (A) shows the case where ends of the distributors have a tweezer-like shape, and (B) shows the case where ends of the distributors have a shape resembling a connecting tube.

In the electrode unit 113 shown in (A) of FIG. 3, a voltage is applied to electrodes 40 through wires 33a and 33b connected respectively to a positive terminal 31a and a negative terminal 31b. Tweezer members 35a and 35b grasp the electrodes 40a and 40b to hold the same steady and apply a voltage thereto to thereby induce an electrochemical reaction between the electrodes 40.

In the electrode unit 113 shown in (B) of FIG. 3, except for the fact that connecting tubes 36a and 36b are used in place of the tweezer members 35a and 35b, all other aspects of the electrode unit 113 of (B) of FIG. 3 are identical to the electrode unit 113 of (A) of FIG. 3. A diameter of the connecting tubes 36a and 36b is slightly greater than that of the electrodes 40 to thereby allow for the insertion of the electrodes 40 in the connecting tubes 36a and 36b. Hence, the electrodes 40 are inserted in the connecting tubes 36a and 36b, and a voltage is applied to the electrodes 40 through wires 34a and 34b connected respectively to an anodic electrode 32a and a cathodic electrodes 32b, thereby inducing an electrochemical reaction between the electrodes 40.

First through fourth embodiments of the present invention in relation to the shape of the electrodes 40 of FIG. 3 will now be described with reference to FIGS. 4 through 7. Electrodes according to the first through fourth embodiments of the present invention may be formed respectively as cable electrodes, straight electrodes, wave electrodes, and coil electrodes. It is to be understood that these embodiments merely illustrate the present invention and are not meant to be restrictive.

An electrode unit for an electrochemical therapy apparatus according to first through fourth embodiments of the present invention includes an anodic electrode and a cathodic electrode in the form of a wire coated with platinum and connected to a distributor. A direct current is flowed between the anodic electrode and cathodic electrode to thereby perform electrochemical therapy.

In the electrochemical therapy apparatus of the present invention, in order to improve an adhesivity and accuracy of a film, a non-equilibrium magnetron sputtering method is used to coat a wire-shaped anodic electrode and cathodic electrode. Considering that the electrodes will be directly contacted to the human body, the electrodes are preferably made of tungsten, which is very strong and difficult to break or otherwise damage during surgery and their surfaces are preferably rough to further improve adhesivity. In addition, it is possible to use an electrode made of titanium, which has a good adherence.

In the non-planar magnetron sputtering method, the flux of a magnetic field is formed such that the movement of plasma in a process chamber is purposely made unstable to maintain non-equilibrium. In the non-equilibrium magnetron sputtering method, a magnet having a larger magnetic field than an internal magnet is mounted to an exterior such that part of the magnetic field affects a coated electrode to realize ionization in the vicinity of the electrode. This improves characteristics of a plating layer. In particular, when the coated electrode is not a planar substrate and is instead in a rough form, a film may be evenly formed over an entire surface.

A thickness of platinum coated on the electrode made of tungsten is preferably 2500–3000 Å. If the thickness of the platinum coated on the electrode is less than 2500 Å, adhesivity is reduced as a result of the thinness of the film. Further, if the thickness of the platinum coated on the electrode exceeds 3000 Å, production unit costs are increased as a result of the high cost of platinum.

Figure 4:
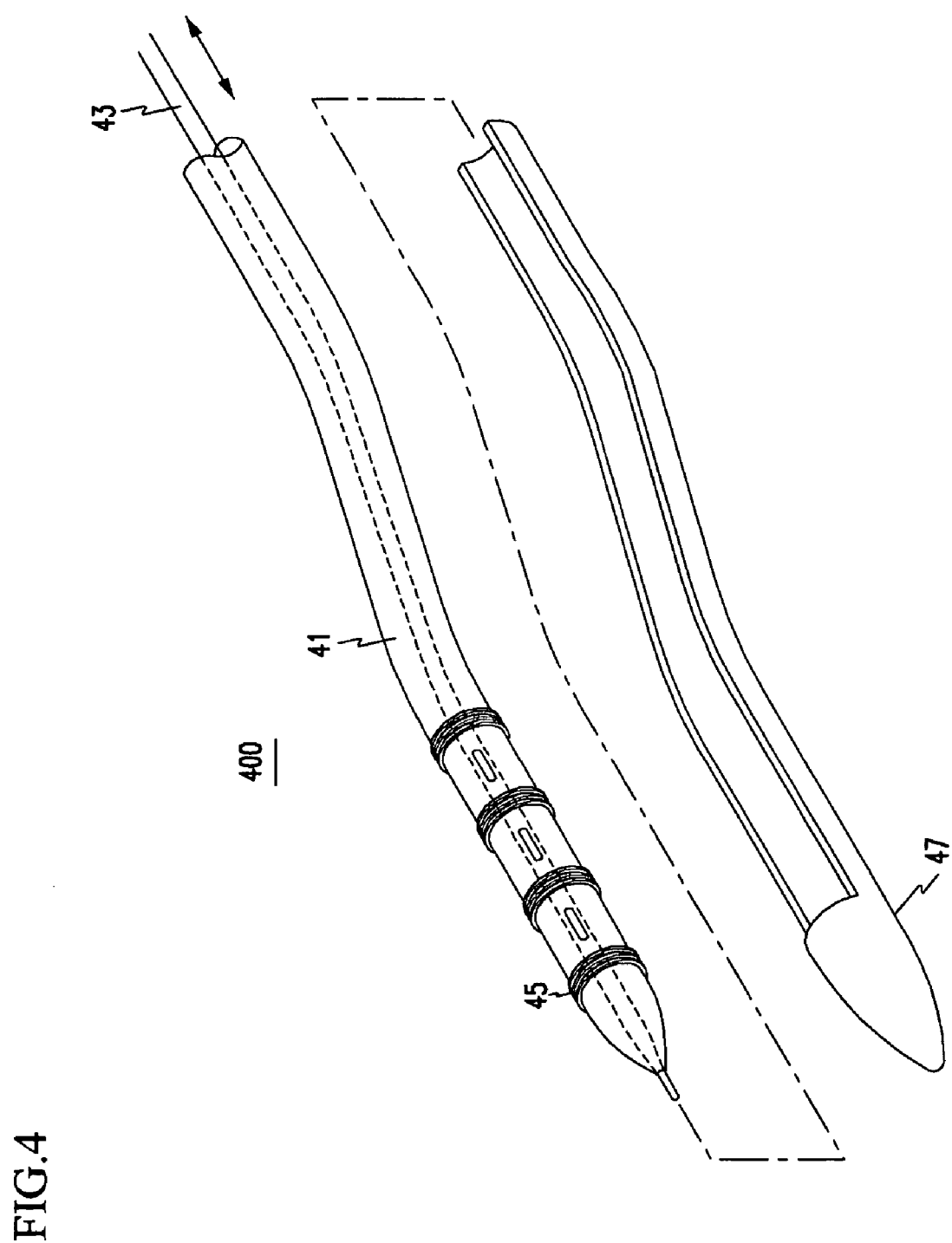
FIG. 4 is an exploded perspective view of an electrode unit of an electrochemical therapy apparatus for curing cancer of the esophagus according to a first embodiment of the present invention.

FIG. 4 is an exploded perspective view of a cable electrode unit of an electrochemical therapy apparatus for curing cancer of the esophagus according to a first embodiment of the present invention. A cable electrode 400 may be used by connection with a distributor that is connected to an anodic electrode and a cathodic electrode, and is inserted in the esophagus, rectum, vagina, uterus, or a blood vessel to treat tumors formed therein. The cable electrode 400 is formed such that an electrode wire 43 that is coated with platinum is moveably inserted in a center of a flexible tube 41, and positive or negative wire ties 45 are mounted at predetermined intervals on the tube 41. The wire ties 45 are formed by wrapping a wire three or four times around the tube 41. With this configuration, the electrode wire 43 may have a positive or negative polarity, and the wire ties 45 may alternate between a positive polarity and a negative polarity.

Further, the above elements are inserted in a guide cap 47, which is formed such that approximately half of the above assembly except for a front end thereof is exposed. Part of the guide cap 47 is removed such that the assembly inserted therein may be freely rotated to adjust an exposed area by the wire ties 45, thereby enabling suitable adjustments of the treatment area to be made.

Figure 5:
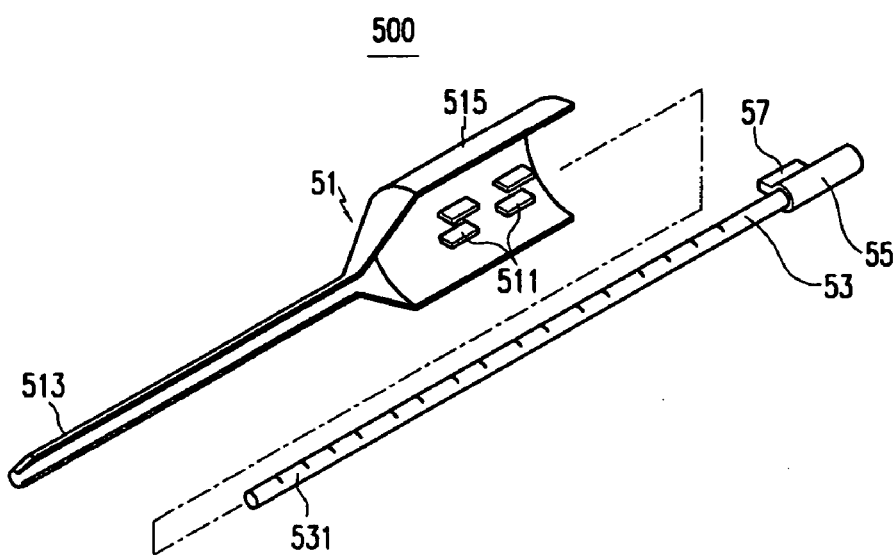
FIG. 5 is a schematic view of an electrode unit of an electrochemical therapy apparatus according to a second embodiment of the present invention.
Figure 5:
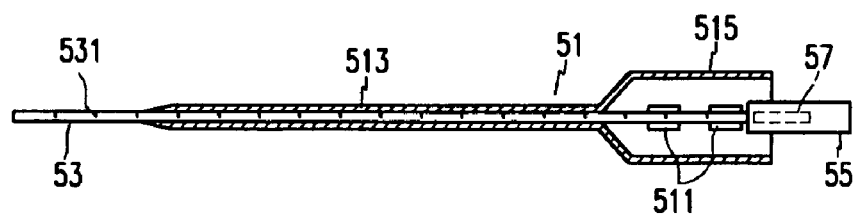

FIG. 5 schematically shows a straight electrode of an electrode unit of an electrochemical therapy apparatus according to a second embodiment of the present invention. In FIG. 5, (A) is an exploded perspective view and (B) is a perspective view showing the electrode unit in an assembled state. Part of a guide cap 51 that surrounds a needle 53 is removed in FIG. 5 to aid in the understanding of the electrode unit. However, it should be understood that the guide cap 51 is actually cylindrical and fully encompasses the needle 53.

In a straight electrode 500 shown in (A) of FIG. 5, a connecting terminal 55 is connected to one end of the needle 53 that is coated with platinum, and the needle 53 is covered with the guide cap 51. The straight electrode 500 can be continuously used at 1000 C. Notches 531 are formed on a surface of the needle 53 such that when inserted in the area of treatment, the insertion depth may be determined. Further, a length of the needle 53 that is suitable for particular sizes and volumes of tumors may be used. To fix the needle 53, the guide cap 51 includes an insulated needle guide 513 made of plastic or another such material and through which the needle 53 passes, and a connecting opening 515.

With reference also to (B) of FIG. 5, connecting protrusions 511 are formed in the connecting opening 515, and a locking protrusion 57 is formed from the connecting terminal 55 corresponding to the connection protrusions 511 to thereby allow for the secure fixing of the needle 53.

Figure 6:
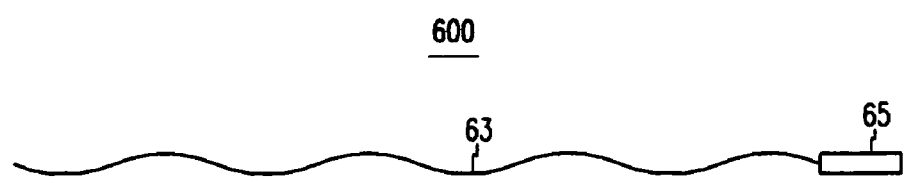
FIG. 6 is a schematic view of an electrode unit of an electrochemical therapy apparatus according to a third embodiment of the present invention.
Figure 7:
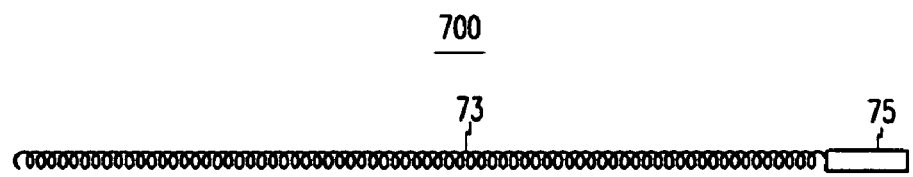
FIG. 7 is a schematic view of an electrode unit of an electrochemical therapy apparatus according to a fourth embodiment of the present invention.

FIGS. 6 and 7 are schematic views respectively of a wave electrode 600 according to a third embodiment of the present invention and a coil electrode 700 according to a fourth embodiment of the present invention.

The wave electrode 600 according to the third embodiment of the present invention shown in FIG. 6 includes a connecting terminal 65 connected to a wave-shaped needle 63 that is coated with platinum. The coil electrode 700 according to the fourth embodiment of the present invention includes a connecting terminal 75 connected to a coil-shaped needle 73.

By modifying the shape of the needle in this manner, the surface area of the electrode contacting the treatment area is increased to further enhance the effectiveness of therapy.

In the first through fourth embodiments of the present invention, one electrode may act to destroy cells in a 1~1.5 cm range. The number of electrodes used may be varied according to tumor size and volume. In order to destroy the tumors easily, the anodic electrodes can be located in the center of the tumors while the cathodic electrodes can be located in the edges of the tumors surrounding the anodic electrodes. In addition, it is possible to insert the anodic electrodes into the center of the tumors while inserting the cathodic electrodes into the normal tissues which are apart from the tumors. The electrodes of the second through fourth embodiments are manufactured in a needle configuration of various lengths and diameters except the electrodes of the first embodiment.

Although not shown, a cross section perpendicular to the lengthwise direction of the needle may be made to various shapes. That is, a structure in the form of a probe may be carved into a surface of the electrode such that a significant amount of electrode charge may be transferred to the tissue of a tumor from the electrode, and a plurality of arcs may be formed on a circumferential surface of a cylindrical electrode to thereby increase a surface cross-sectional area. The shape of the cross section of the needle perpendicular to the lengthwise direction of the needle may be pentagonal, hexagonal, or a radial shape.

An experimental example of the present invention is described below. The experimental example is used to illustrate the present invention and is not meant to be restrictive.

EXPERIMENTAL EXAMPLE

In the experimental example of the present invention, a needle made of tungsten was coated with platinum to manufacture an electrode used for electrochemical therapy. A tungsten wire was submerged for minutes in a diluted hydrochloric acid solution, and was undergone ultrasonic washing using acetone and alcohol for minutes to perform a first cleaning operation. Next, to perform a second cleaning operation of the tungsten wire, a negative voltage of 400–1000V and a pulse voltage of 0.1~0.2 Å was applied for minutes in the process chamber and in an argon gas atmosphere of $6 \times 10^{-2}$ torr to thereby perform glow discharge.

Using the non-equilibrium magnetron sputtering method, the pressure of argon gas with respect to the platinum target was maintained at $2 \times 10^{-3}$ torr in the process chamber, and a voltage of 390V was applied with a current of 1.3 A to perform deposition for 7 minutes. During this process, the evaporation rate of the platinum target was 15 Å/s. The straight electrode manufactured using this method was used to remove tumors.

Data related to tumor size and position were input through the keyboard, and the arithmetic processing circuit of the main controller was driven such that the parameters of current, voltage, and electric charge amount needed to treat tumors were automatically calculated and output using the program stored in the storage unit. These parameters were converted to simulation voltages in the D/A circuit, and these voltages were output to the electrode units through the output drivers of the channels.

The straight electrodes were connected to the connecting tubes of the distributor, and a distance of 0.5~4 cm was maintained between the anodic electrode and cathodic electrode when inserted in the tumor. During this electrochemical treatment process, the current and voltage between the electrodes were transmitted to the main controller through the A/D circuit. The arithmetic processing circuit of the main controller adjusted the driving voltage based on the current and voltage stored in the storage unit such that the voltage and current were uniformly maintained. Tumors were able to be effectively treated using the above electrochemical method.

The electrochemical therapy apparatus of the present invention includes the main computer, storage unit, input and output units, converter, and a plurality of channels and electrode units, and is able to effectively perform electrochemical therapy through the calculation of parameters needed for electrochemical therapy. Accordingly, the present invention may be easily used for patients having malignant tumors that cannot be excised, and patients that show no reaction to or are too weak to utilize the application of radioactive rays or cancer-inhibiting drugs.

In addition, the anodic electrodes and the cathodic electrodes of the electrode units have a high degree of durability as a result of being coated with platinum.

Since the resistance values of the tumor issues are separately measured, and the current or the voltage is controlled, it is possible to destroy the tumor issues easily and to allow the channels not to be confused with other channels, thereby improving the security for curing. In addition, since electrochemical therapy is carried out by connecting electrodes to a plurality of channels, the range of therapy can be widened.

Furthermore, since electrochemical therapy is performed by connecting electrode units to a plurality of channels, treatment is highly effective and the electric signals are electrically isolated by independent driving such that there is no possibility of crossing of wires with other channels, to thereby realize a high degree of safety during treatments.

In the case of the output drivers included in the channels, a constant current or a constant voltage is maintained for a specific time in step pattern, and output is controlled by this pattern such that the effectiveness of therapy is maximized and may be predicted to provide convenience.

By further including the warning unit, users may be cautioned in the case when the circuit of the system is open or short, thereby improving safety during therapy. Also, power supplied to the electrode units may be cutoff during emergencies by including the power cutoff circuit to further improve safety.

Tungsten based electrodes are coated with platinum using the non-equilibrium magnetron sputtering method and its surface is made to be rough, thereby enhancing adhesivity and precision of the platinum.

By including a distributor in the electrode units, connection to the electrodes is more easily accomplished.

Although embodiments of the present invention have been described in detail hereinabove in connection with certain exemplary embodiments, it should be understood that the invention is not limited to the disclosed exemplary embodiments, but, on the contrary is intended to cover various modifications and/or equivalent arrangements included within the spirit and scope of the present invention, as defined in the appended claims.

What is claimed is:

1. An electrochemical therapy apparatus, comprising:
   a main controller for performing calculation processes of parameters for electrochemical therapy;
   a storage unit connected to the main controller, and storing a program for processing the parameters and also storing data related to the parameters;
   an input unit and an output unit connected to the main controller, the output unit displaying or printing data related to the parameters;
   a converter connected to the main controller and converting the parameters output from the main controller into analog values to transmit the parameters as electrical signals for electrochemical therapy, or converting input analog values into digital values and transmitting the digital values as electrical signals to the main controller;
   a plurality of channels connected to the converter to transmit electrical signals, each of the channels operating independently; and
   a plurality of electrode units each connected to one of the channels, and each including an anodic electrode and a cathodic electrode in a wire shape, and that are coated with platinum and between which direct current flows to perform electrochemical therapy;
   wherein each of the channels comprises an output driver which maintains the constant voltage of 2V for one hour and then generates a constant current of 100 mA.

2. The electrochemical therapy apparatus of claim 1, wherein each of the channels further comprises:
   an isolated amplifier, which is electrically isolated, outputs an electrical signal transmitted from the converter to realize independent driving for electrochemical therapy in order to prevent electrical shocking from transmitting to a patient;
   a protection unit connected to the electrode unit and cutting off power when there are abnormalities in the current or voltage applied to the electrode unit from the output driver; and
   a detector connected to the electrode unit, detecting a voltage or a current applied to the electrode unit, and transmitting the voltage or current to the converter;
   wherein the output driver is connected to the isolated amplifier, receives a driving voltage for electrochemical therapy and converts the driving voltage to a direct current.

3. The electrochemical therapy apparatus of claim 1, further comprising a warning unit generating a warning message or warning alarm when an open or short occurs in the electrode units and a corresponding signal is received from the main controller.

4. The electrochemical therapy apparatus of claim 2, wherein the protection unit includes a power cutoff circuit that receives a driving voltage from the corresponding electrode unit, and cuts off power supplied to the electrode unit if any one of a current and voltage between the anodic electrode and the cathodic electrode falls outside of the ranges respectively of 1~300 mA and 1~30V.

5. The electrochemical therapy apparatus of claim 2, wherein the protection unit includes a power cutoff circuit that cuts off power supplied to the corresponding electrode unit when a resistance value, which is obtained by setting as a numerical value a distance between the anodic electrode and the cathodic electrode, exceeds a predetermined value.

6. The electrochemical therapy apparatus of claim 1, wherein the anodic electrodes and the cathodic electrodes are made of tungsten, and surfaces thereof are rough.

7. The electrochemical therapy apparatus of claim 1, wherein at least one of the anodic electrodes and the cathodic electrodes are coated with platinum using a non-equilibrium magnetron sputtering method.

8. The electrochemical therapy apparatus of claim 7, wherein a thickness of the platinum coated on the anodic electrodes and the cathodic electrodes is 2500~3000 Å.

9. The electrochemical therapy apparatus of claim 1, wherein the electrode units each include a distributor connected to the anodic electrodes and the cathodic electrodes.

10. The electrochemical therapy apparatus of claim 9, wherein each of the distributors includes tweezer-like members or connecting tubes at one end thereof and each is connected to the corresponding anodic electrode and cathodic electrode through the tweezer-like members or connecting tubes.

11. The electrochemical therapy apparatus of claim 9, wherein the electrode units further comprise a guide cap that surrounds a distributor-connecting area of the anodic electrode and the cathodic electrode, and exposes an opposite end.

12. The electrochemical therapy apparatus of claim 11, further comprising a flexible tube positioned along a lengthwise direction of the anodic electrode and the cathodic electrode between the anodic electrode and cathodic electrode of the distributor-connecting area and the guide cap, and a plurality of wire ties are formed surrounding an outer circumference of the flexible tube at predetermined intervals, part of the guide cap in the area where the wire ties are formed being cut away.

13. The electrochemical therapy apparatus of claim 12, wherein the wire ties alternately have a positive polarity and a negative polarity formed thereon.

14. The electrochemical therapy apparatus of claim 1, wherein at least one of the anodic electrodes and the cathodic electrodes are wave shaped.

15. The electrochemical therapy apparatus of claim 1, wherein at least one of the anodic electrodes and the cathodic electrodes are coil shaped.

* * * * *